United States Patent
Rey et al.

(10) Patent No.: US 7,890,175 B1
(45) Date of Patent: *Feb. 15, 2011

(54) CONNECTOR ASSEMBLY FOR USE WITH MEDICAL DEVICES

(75) Inventors: Gerry Rey, Buena Park, CA (US); Sandy Damasco, Irvine, CA (US); Majid Ghasiri, Mission Viejo, CA (US)

(73) Assignee: Bal Seal Engineering, Inc., Foothill Ranch, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/895,324

(22) Filed: Sep. 30, 2010

Related U.S. Application Data (63) Continuation of application No. 11/839,103, filed on Aug. 15, 2007, now Pat. No. 7,822,477.

(51) Int. Cl.
  *A61N 1/00* (2006.01)
(52) U.S. Cl. ...................................................... 607/37
(58) Field of Classification Search .................. 607/37; 439/843, 851, 675, 271
  See application file for complete search history.

(56) References Cited

U.S. PATENT DOCUMENTS

| 3,001,170 | A  | 9/1961 | Eyre et al. |
| 4,934,366 | A  | 6/1990 | Truex et al. |
| 6,878,013 | B1 | 4/2005 | Behan |
| 6,895,276 | B2 | 5/2005 | Kast et al. |
| 6,929,517 | B2 | 8/2005 | Tsai |
| 7,003,351 | B2 | 2/2006 | Tvaska et al. |

(Continued)

OTHER PUBLICATIONS

Office Action mailed Apr. 21, 2010 from corresponding U.S Appl. No. 11/839,103.

(Continued)

*Primary Examiner*—George Manuel
*Assistant Examiner*—Robert N Wieland
(74) *Attorney, Agent, or Firm*—Klein, O'Neill & Singh, LLP (57) ABSTRACT

Connector assemblies for use with implantable medical devices having easy to assemble contacts are disclosed. The connector assemblies are generally formed by coupling a plurality of contact housings, sealing rings and leaf spring contact elements to form a connector having a common bore for receiving a medical lead cable. Contact grooves for positioning the leaf spring contact elements are formed in part by assembling multiple components together.

20 Claims, 5 Drawing Sheets

U.S. PATENT DOCUMENTS

| | | |
|---|---|---|
| 7,062,329 B2 | 6/2006 | Ostroff |
| 7,063,563 B1 | 6/2006 | Hsu |
| 7,070,455 B2 | 7/2006 | Balsells |
| 7,083,474 B1 | 8/2006 | Fleck et al. |
| 7,108,549 B2 | 9/2006 | Lyu et al. |
| 7,195,523 B2 | 3/2007 | Naviaux |
| 7,241,180 B1 | 7/2007 | Rentas Torres |
| 7,299,095 B1 | 11/2007 | Barlow et al. |
| 7,326,083 B2 | 2/2008 | Mehdizadeh et al. |
| 7,429,199 B2 | 9/2008 | Burgess |
| 7,510,447 B2 | 3/2009 | Drew |
| 7,526,339 B2 | 4/2009 | Lahti et al. |
| 7,590,451 B2 | 9/2009 | Tronnes et al. |
| 7,682,202 B2 | 3/2010 | Arnholt et al. |
| 7,690,953 B2 | 4/2010 | Boyd et al. |
| 7,711,427 B2 | 5/2010 | Janzig et al. |
| 7,711,428 B2 | 5/2010 | Janzig et al. |
| 7,717,754 B2 | 5/2010 | Ries et al. |
| 7,720,538 B2 | 5/2010 | Janzig et al. |
| 7,758,384 B2 | 7/2010 | Alexander et al. |
| 2007/0100386 A1* | 5/2007 | Tronnes et al. ............ 607/37 |

OTHER PUBLICATIONS

Notice of Allowance mailed Aug. 26, 2010 from corresponding U.S. Appl. No. 11/839,103.

* cited by examiner

CONNECTOR ASSEMBLY FOR USE WITH MEDICAL DEVICES

CROSS-REFERENCE TO RELATED APPLICATION

This is a Continuation application of Ser. No. 11/839,103, filed Aug. 15, 2007 now U.S. Pat. No. 7,822,477, the contents of which are expressly incorporated herein by reference.

FIELD

A connector assembly having one or more conductive elements in spaced-apart configuration is generally discussed herein with particular discussions extended to connector assemblies for use with implantable medical devices having easy to assemble contact elements.

BACKGROUND

Implantable medical devices for providing electrical stimulation to body tissues, for monitoring physiologic conditions, and for providing alternative treatments to drugs are well known in the art. Exemplary implantable medical devices include implantable cardio defibrillators, pacemakers, and programmable neurostimulator pulse generators, which are collectively herein referred to as "implantable medical devices" or IMDs. These IMDs typically incorporate a hermetically sealed device enclosing a power source and electronic circuitry. Connected to the sealed housing, also known as a "can," is a header assembly. The header assembly includes electrical contact elements that are electrically coupled to the electronic circuits or to the power source located inside the can via conductive terminals. The header assembly provides a means for electrically communicating, via an external medical lead cable, the electronic circuits or power source located inside the device to the actual stimulation point.

Industry wide standards have been adopted for, among other things, the dimensions, size, pin spacing, diameter. etc. for the receptacle and the medical lead cable. Furthermore, sufficient electrical contact must be maintained during the life of the implantable medical device, and the medical lead cable for use with the IMD must not disconnect from the receptacle located in the header, yet be detachable for implanting and programming purposes and for replacing the IMD when necessary.

Although prior art connector contacts provide viable options for medical device manufacturers, the overall dimensions of existing receptacles pose manufacturing challenges. Among other things, placing stackable rings in between electrically insulating seals and positioning conductive contact elements in between conductive grooves for forming a receptacle prove costly and time consuming. Accordingly, there is a need for a receptacle that not only meets the challenges associated with implantable applications but is also easier to manufacture than a variety of existing receptacles. There is also a need for a receptacle that is easily adaptable with existing implantable medical devices that are easier to manufacture than a variety of existing implantable medical devices.

Other aspects and features of the receptacles provided herein may be better appreciated as the same become better understood with reference to the specification and claims.

SUMMARY

In accordance with aspects of the present invention, there is provided an implantable medical device comprising a header attached to a sealed housing; a connector assembly disposed in the header comprising a contact housing having portions that overlap with a sealing ring, and a spring contact element disposed in a contact groove defined at least in part by an interior surface of the contact housing and a radially facing wall surface of a shoulder on one of the sealing rings.

In according to another aspect of the present invention, there is provided a connector assembly for use with an implantable medical device comprising: an end cap; a contact housing comprising a bore and comprising a portion that overlaps with the end cap; a sealing ring comprising a shoulder projecting into the bore of the contact housing; a groove disposed between the shoulder of the sealing ring and an inner circumferential surface of the contact housing having a base ring, having a plurality of spaced apart spring fingers extending therefrom, disposed therein.

In yet another aspect of the present invention, there is provided a method of assembling a connector assembly for use with an implantable medical device. The method comprising providing a first contact housing having a slot and an interior surface defining a cavity; inserting a spring contact element comprising a base having a plurality of fingers extending therefrom into the cavity of the first contact housing; inserting a seal ring into the base of the spring contact element; and mounting a second contact housing having a slot and an interior surface defining a cavity around at least a portion of the seal ring.

In one of its broadest scope, the present invention is directed to a connector assembly for use with an implantable medical device that has easy to install contact groove for locating a spring contact element. The contact groove may be formed without using specialty tools or devices.

DETAILED DESCRIPTION

The detailed description set forth below in connection with the appended drawings is intended as a description of the presently preferred embodiments of connector assemblies for electrically communicating with medical leads. The connector assemblies provided in accordance with aspects of the present invention are not intended to represent the only forms in which the present invention may be constructed or utilized.

The description sets forth the features and the steps for constructing and using the connector assemblies of the present invention in connection with the illustrated embodiments. It is to be understood that the same or equivalent functions and structures may be accomplished by different embodiments and are also intended to be encompassed within the spirit and scope of the present invention, especially those incorporating a combination of features shown in the different embodiments included herein. As denoted elsewhere herein, like element numbers are intended to indicate like or similar elements or features.

Figure 1:
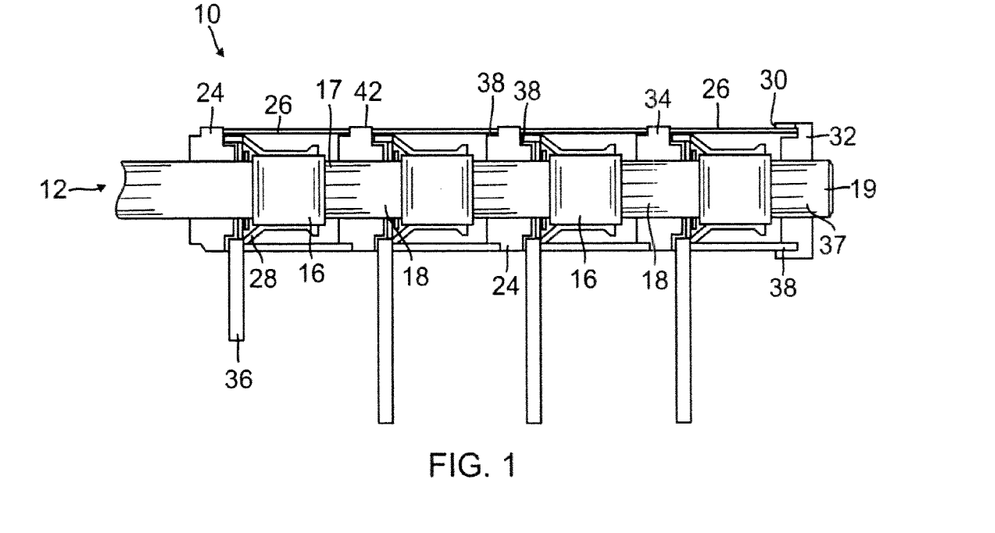
FIG. 1 is a partial cut-away side view of a connector assembly in an assembled state provided in accordance with aspects of the present invention, the connector assembly comprising a plurality of seal rings, contact rings, and leaf spring contact elements.

Referring now to FIG. 1, a partial cut-away view of a connector assembly provided in accordance with aspects of the present invention is shown, which is generally designated 10. The connector assembly 10 is configured to receive a medical lead cable 12, which has a plurality of electrical terminals 16 interposed in between lead insulators 18. The cable 12 comprises a lead body 17 for carrying a plurality of electrode leads from between the proximal end 19 and a distal end (not shown), which has electrode terminals for providing electrical stimulation to the body tissues. The number of electrode leads and corresponding number of electrical terminals can vary depending on the particular implant application, which also determines the number of electrical ring contacts incorporated in the connector assembly 10, as further discussed below. Accordingly, applications of the connector assemblies discussed herein include unipolar, bipolar, and multi-polar applications by simply changing the number of components used to make the connector assembly.

In one exemplary embodiment, the connector assembly 10 comprises a plurality of non-conductive seal rings 24, contact housings 26, and leaf spring contact elements 28. The plurality of seal rings 24, contact housings 26, and leaf spring contact elements 28 form the basic components of the connector assembly 10 of the present embodiment, which has a common bore for receiving the proximal end 19 of the lead cable 12.

Broadly speaking, the seal rings 24 are each configured to seal, along its internal diameter, against the lead cable 12 and, along the outer periphery of its one or more exterior shoulders, adjacent respective contact housing(s) 26, from the external environment. As is readily apparent to a person of ordinary skill in the art in an implant application, bodily fluids should be prevented from traveling along the lead cable 12 into the connector assembly or in through the seams between the contact housing 26 and two adjacent seal rings 24.

The leaf spring, contact elements 28 are each configured to pass an electric signal from a lead 36 located inside an IMD housing or "can" to a corresponding leaf spring contact element 28. The signal is then passed to a corresponding electrical terminal 16 on the lead cable 12 then onto a corresponding electrode lead located inside the lead body 17 and to a corresponding electrode terminal on the distal end of the cable.

In accordance with aspects of the present invention, two sub-classes of seal rings 24 are incorporated, which include an end seal ring 32 and an intermediate seal ring 34. The end seal ring 32 comprises an annular groove 30 adapted to receive an edge of a contact housing 26 and a central opening 37 for receiving an end portion of the lead cable 12. Alternatively, the end seal ring 32 may be sufficiently thick such that the central opening 37 functions as a bore to receive the lead cable 12 but the proximal end is capped to seal the common bore. The intermediate seal ring 34 comprises two external shoulders 38 for projecting into two adjacent bores of two adjacent contact housings 26 and/or a leaf spring contact element 28. The two shoulders project axially from a center section and each includes a radially facing wall surface area. In one embodiment, an intermediate seal ring 34 can be used in place of the end seal ring 32 without deviating from the spirit and scope of the present invention.

Figure 2:
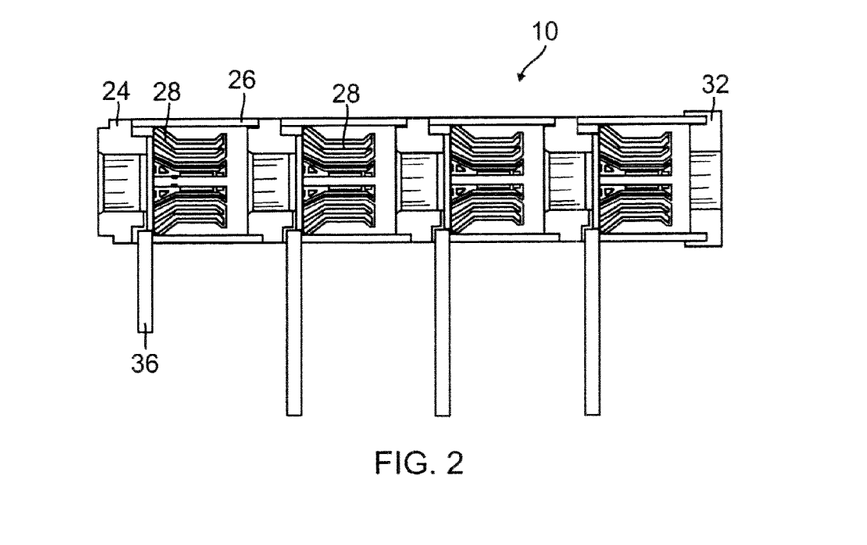
FIG. 2 is a cut-away side view of the connector assembly of FIG. 1 without a medical lead cable.
Figure 3:
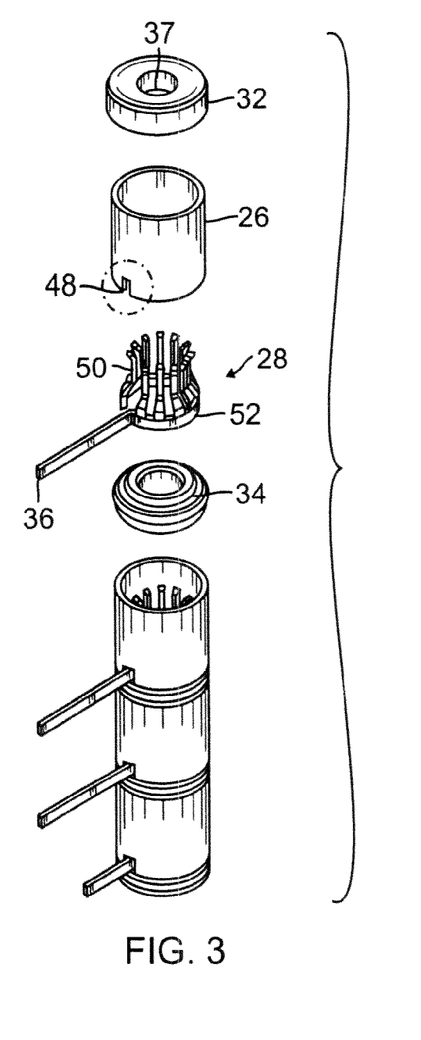
FIG. 3 is a partially exploded view of the connector assembly of FIG. 1.

With specific reference to FIG. 3, in one exemplary embodiment the contact element 28 includes a series of prongs, spring fingers, or leaf springs 50 spaced from each other and extending from a base 52, which in one embodiment comprises an open-ended generally circular ring that is flexible. The base 52 may also be considered an arcuate element that is capable of flexing when receiving a shoulder on a seal ring. When the contact element 28 is located between a seal ring 24 and a contact housing 26, the base 52 serves as a common contact point between the plurality of leaf springs 50 and the lead 36. The base 52 is adapted to form an interference fit into the contact groove 42 located between the seal ring 24 and the housing 26 as shown in FIG. 2. The base 52 may include a compression gap 56 which, as described in more detail below, allows the base 52 to expand when the shoulder 38 of the seal ring 24 is inserted therein.

In one exemplary embodiment, the prongs 50 each includes a generally concave configuration having an apex extending radially inwardly of an imaginary cylinder defined by the base. Each such apex is configured to contact an electrical terminal 16 on the lead cable 12 when the same is inserted into the common bore of the connector assembly 10 to establish electrical communication between the electronic circuitry of the IMD housing and the lead cable 12. As further discussed below, the specific shape of the prongs 50 may be selected to establish one or more than one contact points between each individual prong 50 and the corresponding electrical terminal 16 on the lead cable 12, which may be selected to vary the surface contact area and/or the frictional forces, as is described in more detail below.

A lead 36 may extend from the base 52 of each leaf spring contact element 28 for connection to an input or output of an electrical circuit. The lead 36 may be welded to the contact element 28 and may be made of different materials than the leaf spring contact element 28. Alternately, the lead 36 may be integral with the contact element 28.

The prongs 50 on each contact element 28 are sized so that each is deflected by the lead cable 12 to about 5% and up to about 60% of its total radial deflection. This deflection range ensures a sufficient spring contact force is generated between the prongs 50 and the electric terminals 16 on the lead cable 12 for transferring electric signals between the two. The leaf spring contact elements 28 may be made from a conductive or non-conductive material and may be manufactured by a variety of methods, for example, progressive stamping, hand forming, wire EDM, machining, etching, molding, or a combination thereof. Additionally, the contact elements may incorporate various types of plating to establish, for example, conductivity, non-conductivity, surface hardness and surface finish, among other characteristics. Preferably, the leaf springs are conductive.

Referring again to FIG. 1 in combination with FIG. 3, in one exemplary embodiment, the contact housings 26 are each generally cylindrical in configuration. More preferably, each contact housing 26 has a generally constant inner diameter and outer diameter with two square ends, with normal manufacturing tolerance being acceptable. In other words, the contact housings 26 do not have machined or formed grooves for forming contact grooves therein for accommodating the leaf spring contact elements 28. The housings 26 have a simple profile, which makes manufacturing them and assembling the spring contacts 28 therein easier and therefore more cost effective than grooved housings. The contact grooves 42 are each formed instead by a combination of an adjacent seal ring 24 and the inner surface of a contact housing 26. In one exemplary embodiment, the contact housings 26 each incorporates a notch or slit 48 adapted to accommodate a leaf spring contact element lead 36 when the connector assembly 10 is assembled, as is described in more detail below. While FIG. 1 is a preferred design, alternative contact ring internal geometries are possible in the area of contact with the contact element 28 without compromising ease of assembly for the contact element 28 and contact ring 26. For example, the housings 26 may be made from a conductive and/or a non-conductive material. Further, the housings may be, for example, machined, extruded, formed, molded and/or casted.

Other housing geometries are also contemplated. For example, the housings 26 may have a thicker section so that there are at least two internal diameters. The leaf spring contact element 28 can then be inserted through the larger internal diameter end of the housing 26 until it abuts the shoulder formed at the intersection between the two different internal diameters. Thus, different diameters and undulating internal surfaces for the housings 26 are contemplated. Still alternatively, the plurality of contact housings 26 in a single connector assembly may vary, i.e. are not uniform. For example, it is possible to use a contact housing with different internal diameters at the distal most end of the connector assembly and housings with a smoother contour as shown in FIG. 1 for the remaining housings. If a housing having two different internal diameters at its two ends is used, the seal rings 24 are modified accordingly to engage the different internal diameters of the housing. Thus, the housings 26 provided herein not only can have a smooth internal diameter, but also machined surfaces and undulating surfaces.

Figure 9:
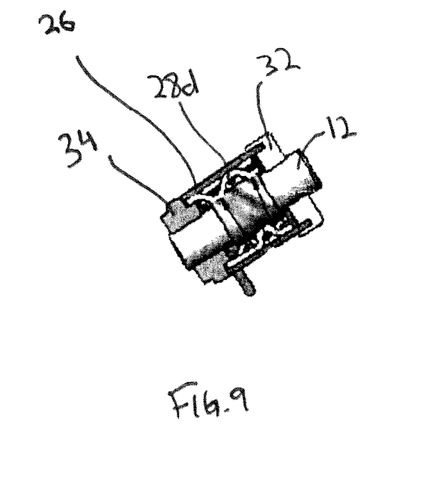
FIGS. 9-10 are isometric cut-away views of alternate embodiments of the present invention incorporating exemplary leaf spring contact elements.
Figure 10:
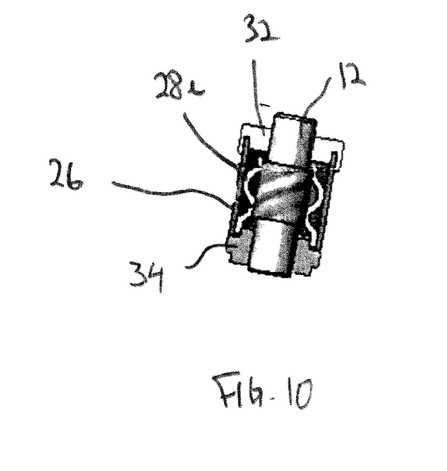

Leaf spring contact elements 28 with various configurations may be used, as shown in FIGS. 5a-8b. FIG. 5a shows the same spring contact element as discussed above with reference to FIG. 5a. As shown in FIG. 5b, a leaf spring contact element 28b has a plurality of prongs 50b with a generally concave configuration and two leads 36b extending from a base 52b, one lead adjacent each edge of a compression gap 56b. As shown in FIGS. 6a and 6b, a leaf spring contact element 28c has a cylindrical wall base 52c extending along a length of the leaf spring contact element and a plurality of concave prongs 50c extending from an edge of the base along the inner circumferential surface of the base 52c. A compression gap 56c may be formed between two adjacent edges of the base 52c and a lead 36c may extend from the base similar to previously described embodiments. With reference to FIGS. 7a, 7b, 8a and 8b, prongs 50d, 50e, 50f and 50g may be generally S-shaped or sine wave shaped to provide at least two contact points. Additionally, the leaf spring contact elements 28d, 28e, 28f and 28g may have one lead 36d, 36g or two leads 36e, 36f. As further shown in FIGS. 9 and 10, the S-shaped adjacent prongs may have their peaks and valleys staggered with respect to each other (FIG. 9) or aligned with each other (FIG. 10).

In accordance with one aspect of the present invention and looking at the connector from the right side of FIG. 1, a method is provided for assembling a plurality of components to form a connector assembly comprising engaging a first seal ring 24, which may be an end seal ring 32 or an intermediate seal ring 34 to a first contact housing 26. A first leaf spring contact element 28 is then placed into the bore of the first housing such that the lead 36 of the contact element protrudes from the housing at the slit 48. The slit 48 fixes the angular alignment between the contact housing 26 and the contact element 28 and provides an access point for electrical communication between circuits inside an IMD housing and the prongs 50 of the contact element. A second seal ring 34 is then connected to the contact housing 26 such that the shoulder 38 of the seal ring is located within an inner circumference of the base 52 of the contact element 28. As noted above, the compression gap 56 allows the base to expand to ensure sufficient contact with the seal ring. With reference to FIGS. 2 and 3 in addition to FIG. 1, when a seal ring 24 engages the contact element 28, the base 52 of the contact element is located in a contact groove 42 formed between the seal ring 24 and the contact housing 26. The method further comprises the steps of adding other seal rings, contact housings, and leaf spring contact elements to form a connector assembly having a desired number of contact grooves for accommodating a desired number of contact elements. More preferably, the method further comprises the steps of assembling a connector assembly without having to use a specialty tool, or some other means to manipulate, compress, bend, or distort a leaf spring contact element to fit within a contact groove. The assembled connector assembly is then placed into a mold cavity and over-molded with an implantable grade polymer or elastomer, such as silicone. The connector assembly can also be inserted into a pre-molded header, which resembles a housing having a cavity for receiving the connector assembly and one or more openings for placing the connector assembly into the pre-molded header. The one or more openings are then back-filled or sealed, typically after attaching or welding the leads from the sealed housing to the contact housings, to complete the assembly. Alternatively, the connector assembly 10 may be assembled starting from the left side of the connector, i.e., starting from the left side of FIG. 1.

In accordance with other aspects of the present invention, an alternative method is provided for assembling a connector assembly in which a dowel or assembly pin (not shown) is used, which resembles the proximal end 19 of the lead cable 12 shown in FIG. 1. The assembly pin (not shown) is used to construct the connector assembly 10 by first placing an end seal ring 32 on an end of the assembly pin and then subsequently placing other components on the pin and then sliding them to engage with the earlier placed components as described above. The assembled components. i.e., the connector assembly, may then be secured by placing the same inside a cavity of a header and over-molding the assembly with an implantable grade polymer or elastomer.

Referring again to FIG. 2, the seal rings 24 of the present embodiment, except for the end seal ring 32, are each symmetrical about a centerline drawn perpendicular to the axis defined by the cable 12 and through the center of the seal ring. However, non-symmetry or other configurations are possible so long as a contact groove for accommodating a spring contact is formed at least in part by engaging the housing 26 with an adjacent seal ring 24. Furthermore, while the seal rings 24 of the present embodiment are shown each comprising an internal surface for sealing against the lead cable 12, two or more projections may be incorporated for sealing against a lead cable without deviating from the spirit and scope of the present invention. Still furthermore, part of the seal ring that projects into the bore of a contact housing can be made separately. In other words, a seal ring may be made by co-molding or over-molding two separate components.

Following assembly of the various components to form the connector assembly 10 shown in FIG. 2, the connector assembly is encased inside an implantable elastomer or polymer layer, as previously discussed. The connector assembly 10 is preferably molded with an assembly pin located inside the common bore to ensure alignment, both radially and axially, of the various connector components. The encased connector may be referred to as a connector header, for placing on a can or sealed housing of an IMD.

Figure 4:
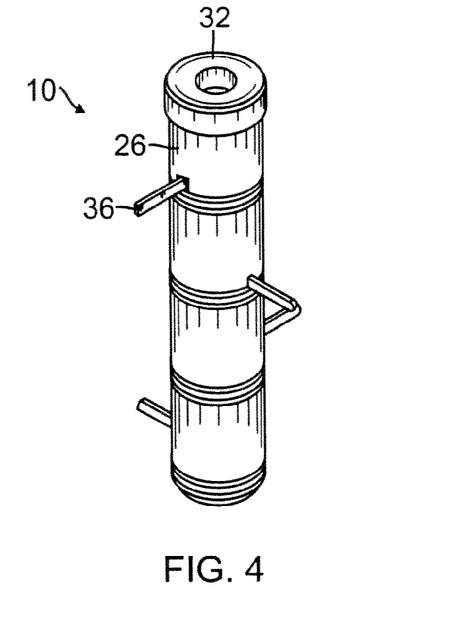
FIG. 4 is a perspective view of an alternate embodiment of a connector assembly provided in accordance with aspects of the present invention showing adjacent leads oriented at different angles from one another.
Figure 5A:
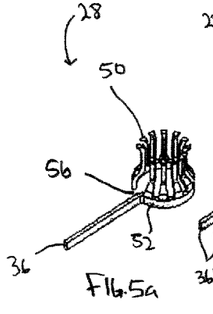
FIGS. 5-8 are perspective views of various leaf spring contact elements provided in accordance with aspects of the present invention.
Figure 5B:
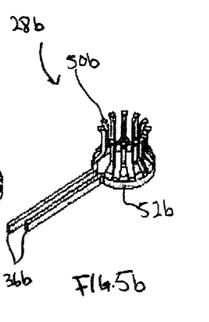
Figures 6A, 6B:
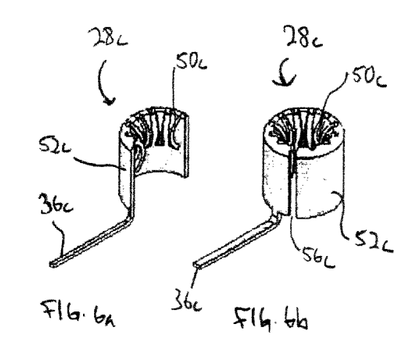
Figures 7A, 7B, 8A:
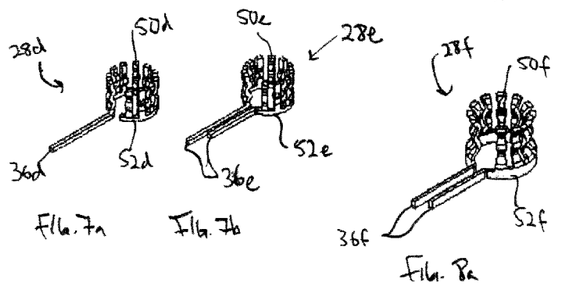
Figure 8B:
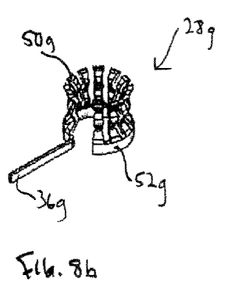

FIG. 4 is a fully assembled view of the connector assembly 10 of FIGS. 1-3, but with the leads oriented differently for a different IMD application. As shown in FIG. 4, adjacent leads 36 protruding from the housings 26 may be oriented perpendicularly to each other. However, the leads 36 may also protrude at acute and/or obtuse angles from each other and the degree of the angles may vary along the length of the electrical connector 10. Still alternatively, the leads may aligned along a generally constant plane.

Figure 11:
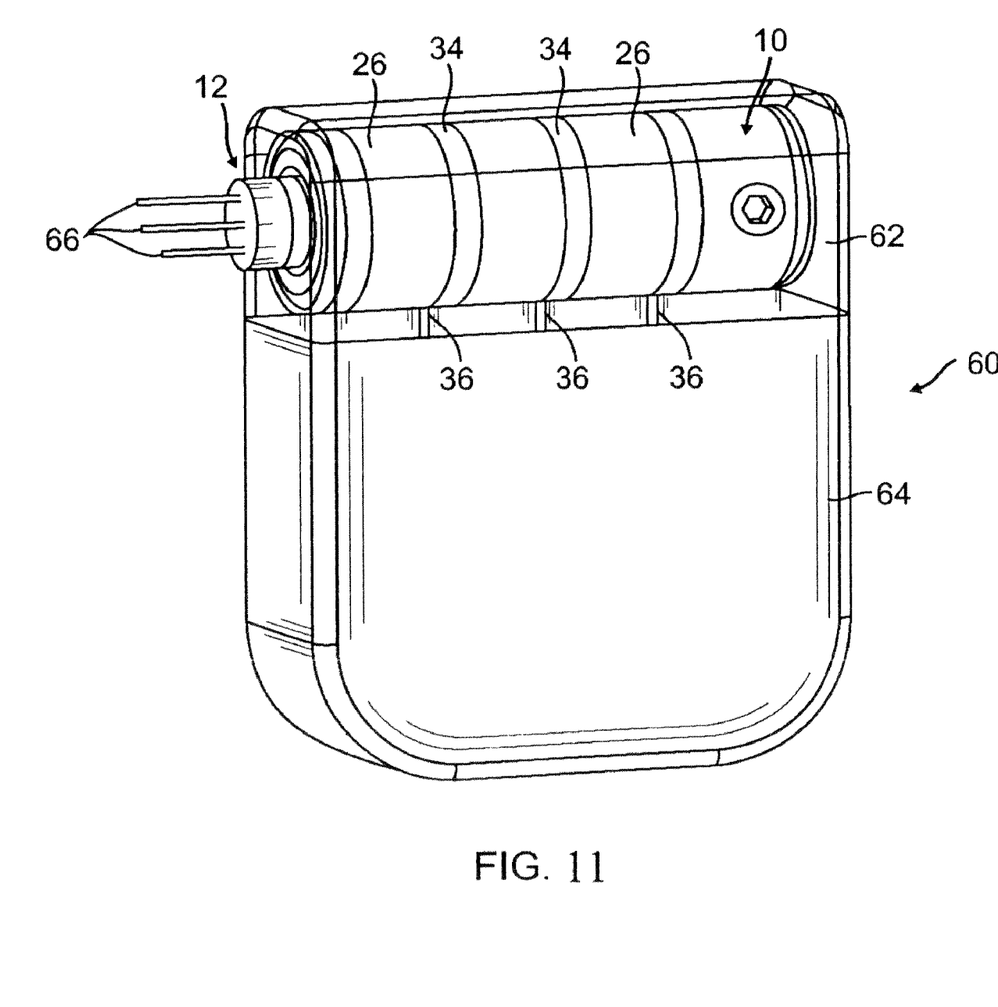
FIG. 11 is an isometric view of an implantable medical device incorporating a connector assembly in accordance with aspects of the present invention in a header.

Referring now to FIG. 11, an IMD 60 incorporating a connector assembly 10 provided in accordance with aspects of the present invention is shown. The connector assembly 10 is shown mounted in a header 62, which is shown as a transparent material or structure for purposes of discussion only. In practice, the overcoat or over-molding layer is more commonly semi-opaque. The header 58 is situated over a can 64, which is hermetically sealed with a power source and electronic circuits. A lead cable 12 is shown inserted into the common bore of the connector assembly 10. Three electrode leads 66 are shown exposed near the opening of the header for illustration purposes. In practice, the lead cable extends to a distal end, which has electrode terminals for providing electrical stimulation to the body tissues or probes for monitoring and/or diagnostics. As previously discussed, the IMD can be any one of plurality of IMDs for medical treatment, monitoring, or diagnostics.

Also shown in FIG. 11 are leads 36 extending from the lead spring contact elements 26. Although a single connector assembly 10 is shown inside the header 62, two or more connector assemblies 10 may be used if desired depending on the particular implant application. If two or more connector assemblies are used, they may be stacked side-by-side or on top of one another.

Although limited preferred embodiments and methods for making and using connector assemblies provided in accordance with aspects of the present invention have been specifically described and illustrated, many modifications and variations will be apparent to those skilled in the art. For example, various material changes may be used, incorporating different mechanical engagement means to attach the various components to one another, making use of two or more different materials or composites, making a sealing ring from multiple pieces rather than a singularly molded piece, etc. Accordingly, it is to be understood that the connector assemblies constructed according to principles of this invention may be embodied in other than as specifically described herein. The invention is also defined in the following claims.

What is claimed is:

1. An implantable medical device comprising a header attached to a sealed housing; a connector assembly disposed in the header comprising a contact housing having portions that overlap with a sealing ring, and a spring contact element comprising spaced apart contact fingers disposed in a contact groove defined at least in part by an interior surface of the contact housing and wherein the spring contact element comprises a lead terminal comprising a lead end and wherein the lead end projects radially away from the contact housing such that the lead end is spaced apart from the contact housing.

2. The implantable medical device of claim, wherein the spring contact element comprises an arcuate ring comprising a gap, said arcuate ring being disposed in the contact groove.

3. The implantable medical device of claim 2, wherein the spaced apart contact fingers extend from the arcuate ring.

4. The implantable medical device of claim 3, wherein the spaced apart contact fingers each comprises an apex configured to contact with a lead cable.

5. The implantable medical device of claim 1, further comprising a slot in the contact housing.

6. The implantable medical device of claim 5, wherein the lead terminal entends through the slot of the contact housing.

7. The implantable medical device of claim 1, further comprising a second contact housing comprising an opening; said opening surrounding at least a portion of the sealing ring.

8. The implantable medical device of claim 1, further comprising a common bore and a lead cable positioned in the common bore.

9. A connector assembly for use with an implantable medical device comprising:
a contact housing comprising a bore and comprising a portion that overlaps with a sealing ring comprising a shoulder;
a spring contact element comprising a base ring having a plurality of spaced apart spring fingers extending therefrom in mechanical contact with the contact housing; and
wherein the shoulder projects, at least in part, into the base ring of the spring contact element.

10. The implantable medical device of claim 9, wherein said base ring comprises a gap.

11. The implantable medical device of claim 10, wherein the spring fingers each comprises at least one apex configured to contact with a lead cable.

12. The implantable medical device of claim 9, further comprising a lead terminal extending from the base ring.

13. The implantable medical device of claim 9, further comprising a slot in the contact housing.

14. The implantable medical device of claim 13, further comprising a lead terminal entending through the slot and in contact with the base ring.

15. The implantable medical device of claim 9, further comprising a second contact housing comprising an opening: said opening surrounding at least a portion of the sealing ring.

16. The implantable medical device of claim 9, further comprising a common bore and a lead cable positioned in the common bore.

17. A method of assembling a connector assembly for use with an implantable medical device comprising:
providing a first contact housing having an interior surface defining a cavity;
inserting a spring contact element comprising a base having spaced apart contact fingers extending therefrom into the cavity of the first contact housing;
inserting a shoulder of a seal ring into the base of the spring contact element; and
placing a second contact housing in mechanical contact with at east a portion of the seal ring.

18. The method of claim 17, wherein the base of the spring contact element comprises a gap.

19. The method of claim 17, further comprising the step of aligning a lead terminal with a slot formed on the first contact housing.

20. The method of claim 17, wherein the connector assembly comprises a common bore, and wherein a lead cable is positioned in the common bore.

* * * * *